United States Patent
Baldock

(10) Patent No.: US 8,168,849 B2
(45) Date of Patent: May 1, 2012

(54) METHOD OF MAKING A BANDAGE

(75) Inventor: David Timothy Baldock, Nr Newark (GB)

(73) Assignee: Laboratoires Urgo SAS, Chenove (FR)

( * ) Notice: Subject to any disclaimer, the term of this patent is extended or adjusted under 35 U.S.C. 154(b) by 911 days.

(21) Appl. No.: 12/089,332

(22) PCT Filed: Oct. 6, 2006

(86) PCT No.: PCT/GB2006/003724
§ 371 (c)(1),
(2), (4) Date: Apr. 4, 2008

(87) PCT Pub. No.: WO2007/039756
PCT Pub. Date: Apr. 12, 2007

(65) Prior Publication Data
US 2008/0234618 A1    Sep. 25, 2008

(30) Foreign Application Priority Data

Oct. 6, 2005 (GB) .................................. 0520336.9

(51) Int. Cl.
*A61F 13/00* (2006.01)
(52) U.S. Cl. .................................... 602/41; 602/44
(58) Field of Classification Search ............... 602/41–54
See application file for complete search history.

(56) References Cited

U.S. PATENT DOCUMENTS

| | | | |
|---|---|---|---|
| 4,414,268 A * | 11/1983 | Baldwin | 442/81 |
| 4,643,180 A | 2/1987 | Feld et al. | |
| 5,009,890 A | 4/1991 | DiPippo | |
| 5,843,523 A | 12/1998 | Mazza et al. | |
| 6,071,549 A | 6/2000 | Hansen | |
| 6,503,524 B1 | 1/2003 | Tyrrell et al. | |
| 6,521,339 B1 * | 2/2003 | Hansen et al. | 428/378 |
| 6,599,521 B1 | 7/2003 | Resheski-Wedepohl et al. | |
| 2004/0053856 A1 | 3/2004 | Resheski-Wedepohl et al. | |
| 2004/0259445 A1 | 12/2004 | Hilfenhaus et al. | |

FOREIGN PATENT DOCUMENTS

| | | |
|---|---|---|
| AT | 310 952 B | 10/1973 |
| EP | 0 531 096 A3 | 3/1993 |
| EP | 1 287 836 A3 | 7/2003 |
| GB | 890682 | 3/1962 |

* cited by examiner

*Primary Examiner* — Michael A. Brown
(74) *Attorney, Agent, or Firm* — Alan G. Towner, Esq.; Matthew W. Gordon, Esq.; Pietragallo Gordon Alfano Bosick & Raspanti, LLP

(57) ABSTRACT

The present invention provides a method of making a bandage from a fabric such as a knitted fabric, for example. The fabric is steamed, sprayed with a solution containing an antibacterial/antimicrobial agent in a spraying chamber 28 and then dried in a drying chamber 40.

28 Claims, 1 Drawing Sheet

METHOD OF MAKING A BANDAGE

CROSS-REFERENCE TO RELATED APPLICATIONS

Figure 1:
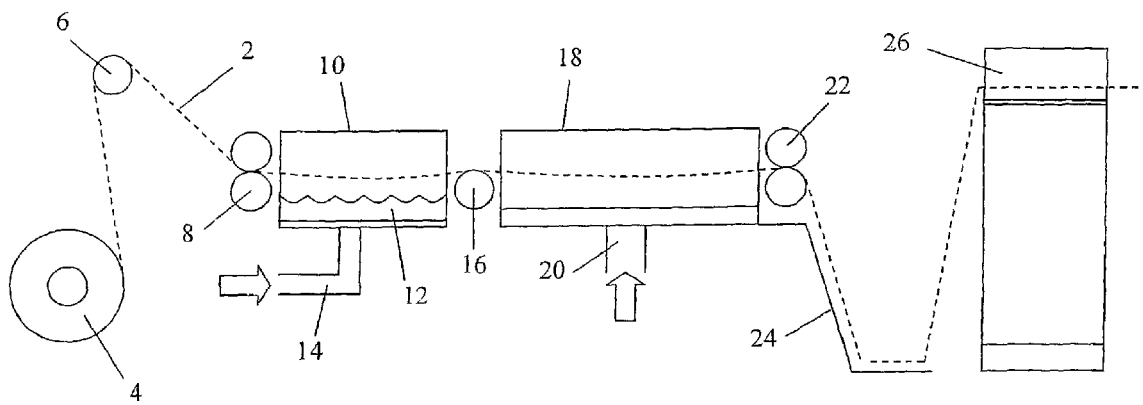

This application is a U.S. National Stage Application under 35 U.S.C. Section 371 of PCT International Application No. PCT/GB2006/003724, filed Oct. 6, 2006 which is incorporated herein by reference as if set forth in its entirety.

TECHNICAL FIELD

The present invention relates to a method of making a bandage, and in particular a knitted bandage that incorporates an antibacterial/antimicrobial agent.

BACKGROUND ART

Bandages can be formed from a variety of different fabrics including inter alia knitted fabrics made using a knitting or crocheting process, woven fabrics, non woven fabrics and fabrics made using an "air jet" weaving process.

Knitted bandages are made from lengths of knitted fabric that are subsequently processed by steaming and drying.

The knitted fabric is produced using a knitting machine having a knitting head that includes a number of needles depending on the width of the fabric. The knitting head knits together yarns of material to form a fabric that includes warp yarns running longitudinally along the length of the fabric and weft yarns that also run generally longitudinally along the length of the fabric but which also meander transversely across the width of the fabric across two or more of the warp yarns. This is in contrast to woven fabrics where the weft yarns normally run transversely across the full width of the fabric. The meandering arrangement of the weft yarns means that the knitted fabric has the ability to stretch in the transverse direction without the need to make the weft yarns from a material having any degree of elasticity.

The yarns can be made of any suitable material and have any size or weight per unit length (sometimes referred to as the count, denier or tex) depending on the desired properties of the finished knitted bandage. Examples of knitted fabrics are set out in Table 1 below.

The knitted fabric is usually gathered and stored as a roll and then subsequently processed using the apparatus shown schematically in FIG. 1.

The length of knitted fabric 2 is fed from a roll 4 over a roller 6 and between a pair of input feed rollers 8 operating at a given rotational speed. The input feed rollers 8 move the length of knitted fabric into a steaming chamber 10. The steaming chamber 10 contains a reservoir 12 that is supplied with softened water through a water inlet pipe 14. A heating element (not shown) is used to heat the water in the reservoir 12 and keeps it at a rolling boil. The length of knitted fabric 2 moves through the steaming chamber 10 above the reservoir 12 where it is exposed to the steam coming from the surface of the boiling water. The exposure to the steam causes any nylon (polyamide) warp yarns and/or any elastomeric warp yarns in the knitted fabric to shrink slightly in the longitudinal direction. This is sometimes referred to as the "relaxation step" because the warp yarns are placed in tension when they are supplied to the knitting head and the exposure to the steam allows the knitted fabric to relax and shrink back to a state where the warp yarns can provide some stretch or elasticity in the finished knitted bandage. The speed of rotation of the input feed rollers 8 is selected so that the travel time of the knitted fabric through the steaming chamber 10 (in other words the time taken for one part of the length of knitted fabric to pass through the steaming chamber 10 from one side to the other) is such that the nylon (polyamide) and/or elastomeric warp yarns are allowed to relax sufficiently for the finished knitted bandage to have the desired amount of stretch or elasticity.

At the output end of the steaming chamber 10, the length of knitted fabric passes over an intermediate feed roller 16 which is optionally driven and into a drying chamber 18. The purpose of the drying chamber 18 is to remove the moisture that is absorbed by the knitted fabric during the steaming process.

Air is supplied though an air inlet pipe 20 before being heated by a heater unit (not shown) and fed into the drying chamber 18. The heater unit has three separate heater elements (not shown) and the temperature of the air inside the drying chamber 18 is determined by switching on one, two or all three of the heater elements. The amount of air that is supplied through the air inlet pipe 20 and into the interior of the drying chamber 18 can be controlled using a vent that can

TABLE 1

| Example Number | Warp yarns | | | Weft yarns | | |
| --- | --- | --- | --- | --- | --- | --- |
| | Material | (Number of ends/cm) | Count | Material | (Number of ends/cm) | Count |
| 1 | nylon (polyamide) | 1.8 +/− 10% | 2/78/24 | viscose (cellulose) | 3.7 +/− 10% | 30s |
| | viscose (cellulose) | 1.7 +/− 10% | 30s | | | |
| 2 | elastomeric yarn | 3.0 +/− 10% | | viscose (cellulose) | 5.5 +/− 10% | 24s |
| | viscose (cellulose) | 5.9 +/− 10% | 24s | | | |
| 3 | elastomeric yarn | 2.9 +/− 10% | | viscose (cellulose) | 5.5 +/− 10% | 24s |
| | Viscose (cellulose) | 5.6 +/− 10% | 24s | | | |
| | Nylon (polyamide) | 0.1 +/− 10% | 2/78/20 | | | | be opened or closed to a specified degree of angle. Outlet vanes can be provided to make sure the hot air is evenly distributed through the inside of the drying chamber 18.

Typical processing parameters for Examples 1 and 2 are set out in Table 2 below. However, the exact temperature inside the drying chamber 18 and the travel times of the length of knitted fabric through the steaming and drying chambers will depend on the particular knitted fabric and on the desired properties of the finished knitted bandage.

TABLE 2

| Example Number | Total travel time through steaming and drying chambers (seconds) | Travel time through drying chamber (seconds) | Temperature in steaming chamber (° C.) | Temperature in drying chamber (° C.) |
|---|---|---|---|---|
| 1 | 7.5 to 8.5 | 4.8 to 5.8 | 86 | 68 (1 heater element; air intake pipe vent 75° open) |
| 2 | 4.5 to 6.0 | 2.9 to 4.0 | 86 | 68 (1 heater element; air intake pipe vent 75° open) |

A pair of output feed rollers 22 are positioned at the output end of the drying chamber 18 and operate at a given rotational speed. As shown in FIG. 1, there is no tension in the length of knitted fabric 2 as it passes through the steaming chamber 10 and the drying chamber 18 so that any shrinkage or relaxation of the knitted fabric in the steaming chamber can be easily accommodated. This lack of tension in the length of knitted fabric 2 is maintained by running the output feed rollers 22 at a rotational speed that is slightly less than the rotation speed of the input feed rollers 8.

The output feed rollers 22 move the length of knitted fabric into a collecting trough 24 before it is taken up and fed into a rolling machine 26. The rolling machine 26 rolls the processed knitted fabric and cuts it into shorter lengths so that the finished knitted bandages can be packaged. A suitable rolling system would consist of:
  (i) Type TAD shrinking and finishing machine
  (ii) Type 7.10 automatic winding rolling machine
These are made and supplied by IVF Technology AG, CH-8212, Neuhausen, Switzerland.

The input, intermediate and output feed rollers 8, 16 and 22 can be stopped and started manually by an operator or automatically with the rolling machine, for example. During the period of time when the input, intermediate and output feed rollers 8, 16 and 22 are not being driven and the length of knitted fabric 2 is stationary, the drying chamber 18 can be opened or vented to allow the hot air to escape so that the length of the knitted fabric within the drying chamber is not burnt or scorched.

The advantages of giving antibacterial and antimicrobial properties to fabrics are known. For example, WO 2005/038122 describes a method of preparing a fabric containing silver having antibacterial properties. The method includes the following steps of (i) preparing a solution containing $H_4Ag_2O_6$, (ii) impregnating, leaching, spraying or coating the fabric with the solution, and (iii) drying the wet fabric. When tested with a cotton unwoven textile the amount of silver in the dried fabric was found to vary between 2.3 and 86.8 μg/cm². Antibacterial reduction of *Staphylococcus aureus* was shown to vary between 97.71% and 100.00% depending on the particular sample used.

SUMMARY OF THE INVENTION

The present invention provides a method of making a bandage from a fabric including the steps of steaming the fabric, spraying the fabric with a solution containing an antibacterial/antimicrobial agent, and drying the fabric.

It is already known to give antibacterial and antimicrobial properties to fabric bandages by spraying them with a solution of an antibacterial and antimicrobial agent. Although it is not intended that this invention should in any way be limited by theoretical observations, it is believed that the surprising success of the spraying process of the invention is a consequence of the fact that the spraying of the antibacterial/antimicrobial agent is directly onto fabric that has been wetted by steaming. This may be because the spraying onto the wetted fabric avoids the creation of droplets of the sprayed agent on the surface of the fabric, and encourages a more immediate and uniform wetting. It is believed that the steaming also has the unexpected advantage of improving the fixing of the antibacterial/antimicrobial agent to the fabric. If the fabric is a knitted fabric then the steaming will also provide the necessary degree of relaxation mentioned above.

The bandage can be formed from a variety of different fabrics including inter alia knitted fabrics made using a knitting or crocheting process, woven fabrics, non woven fabrics and fabrics made using an "air jet" weaving process. A knitted fabric is generally preferred and may be the same as, or broadly similar to, the knitted fabrics described above with reference to Table 1.

The fabric can be sprayed with a solution containing silver, for example. However, any suitable solution that includes an antibacterial and/or antimicrobial agent can be used. The fabric is preferably sprayed to give a coating of antibacterial/antimicrobial agent of from about 0.175 to about 0.6 grams per kilogram weight of the fabric, and most preferably of from about 0.2 to about 0.4 grams per kilogram weight of the fabric. The active constituent of the antibacterial/antimicrobial agent, which can be silver, is in an amount of 0.2 to about 2.1 mg/m², and most preferably from about 0.4 to about 1.6 mg/m². The solution is preferably a non-leaching solution such that the antibacterial/antimicrobial agent is retained within the fabric of the bandage during use. It is normally preferred that the addition of the solution has no material effect on the properties of the fabric such as its stretch or elasticity, for example.

During the drying step, each part of the fabric is preferably dried at a temperature of between about 80° C. and about 100° C. for a certain period of time depending on the type of fabric. The temperature is more preferably about 90° C.

If the fabric includes any warp yarns having some degree of elasticity (such as nylon (polyamide) warp yarns or elastomeric warp yarns, for example) that were knitted or woven under tension then the process of steaming the fabric causes these warp yarns to shrink back and relax. This provides the bandage with some stretch or elasticity in the direction running parallel to the warp yarns.

The present invention further includes an apparatus for making a bandage from a fabric, the apparatus comprising a spraying chamber containing one or more spray guns for spraying the fabric with a solution containing an antibacterial/antimicrobial agent, a steaming chamber for steaming the fabric before it is sprayed, and a drying chamber for drying the fabric after it has been sprayed.

The present invention further includes a bandage consisting of a fabric wherein the fabric contains an amount of antibacterial/antimicrobial agent of from about 0.175 to about 0.6 grams per kilogram weight of the fabric, and most preferably from about 0.2 to about 0.4 grams per kilogram weight of the fabric. The amount of the active constituent of the antibacterial/antimicrobial agent, which can be silver, is preferably from about 0.2 to about 2.1 mg/m$^2$, and most preferably from about 0.4 to about 1.6 mg/m$^2$. This is significantly less than the amounts of antibacterial/antimicrobial agent used in WO 2005/038122 but still results in excellent reductions in bacterium such as *Staphylococcus aureus*, *Escherichia coli* 0157, *Proteus vulgaris* and *Pseudomonas aeruginosa*.

A further bandage may consist of a fabric containing an antibacterial/antimicrobial agent having an active constituent (optionally silver) wherein the amount of the active constituent is from about 0.2 to about 2.1 mg/m$^2$, and most preferably from about 0.4 to about 1.6 mg/m$^2$. The amount of antibacterial/antimicrobial agent is preferably of from about 0.175 to about 0.6 grams per kilogram weight of the fabric, and most preferably from about 0.2 to about 0.4 grams per kilogram weight of the fabric.

In either case the fabric can be sprayed with a solution containing an antibacterial/antimicrobial agent and then optionally dried. The fabric can be steamed before being sprayed. The antibacterial/antimicrobial agent can also be applied to the fabric using other methods such as by immersion of the fabric in a heated solution, optionally at a much greater concentration.

The bandage is not intended to be used directly on broken skin or wounds (in other words as a primary dressing) but is used on top of a dressing or sub-bandage wadding or the like to provide an effective barrier layer against bacterial and microbial infections entering or leaving the dressed wound.

DRAWINGS

Figure 2:
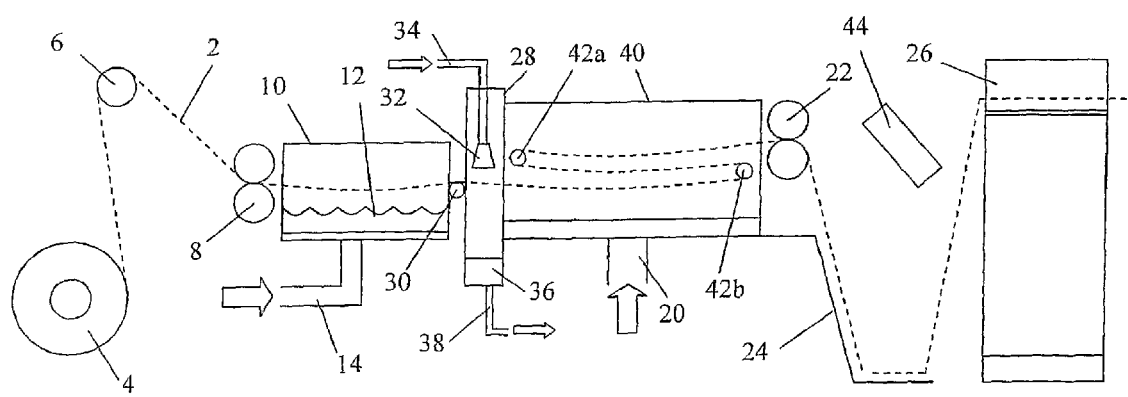

FIG. 1 is a schematic drawing showing a known apparatus for processing a knitted fabric; and FIG. 2 is a schematic drawing showing an apparatus for carrying out the method according to the present invention.

The apparatus shown in FIG. 2 is similar to the known apparatus shown in FIG. 1 and the same reference numerals are used for like parts.

A length of knitted fabric 2 of a type set out in Table 1 above is fed from a roll 4 over a roller 6 and between a pair of input feed rollers 8 operating at a given rotational speed. The input feed rollers 8 move the length of knitted fabric into a steaming chamber 10. The steaming chamber 10 contains a reservoir 12 that is supplied with softened water through a water inlet pipe 14. A heating element (not shown) is used to heat the water in the reservoir 12 and keeps it at a rolling boil. The length of knitted fabric 2 moves through the steaming chamber 10 above the reservoir 12 where it is exposed to the steam coming from the surface of the boiling water. The exposure to the steam causes any nylon (polyamide) warp yarns and/or any elastomeric warp yarns in the knitted fabric to shrink slightly in the longitudinal direction. The speed of rotation of the input feed rollers 8 is selected so that the travel time of the knitted fabric through the steaming chamber 10 is such that the nylon polyamide) and/or elastomeric warp yarns are allowed to relax sufficiently for the finished knitted bandage to have the desired amount of stretch or elasticity.

The length of knitted fabric then passes into a spraying chamber 28 over an intermediate feed roller 30 which is optionally driven. The spraying chamber 28 is an enclosed unit. Two spray guns 32 for compressed air spraying (such as automatic RA 2 spray guns supplied by Charvo Ltd., Skipton, North Yorkshire, UK) are positioned above the length of knitted fabric and adapted to spray a solution down onto the top side of the knitted fabric as it passes through the spraying chamber 28. A second set of spray guns (not shown) can be positioned below the length of knitted fabric and adapted to spray the same solution up onto the bottom side of the knitted fabric as it passes thorough the spraying chamber 28. The spray guns 32 can be synchronised with the rest of the steaming and drying apparatus so that the solution is only sprayed onto the knitted fabric when it is being driven through the spraying chamber 28 by the input feed roller 8 and the intermediate feed roller 30. The solution is supplied to the spray guns 32 from an external canister (not shown) through a solution inlet pipe 34. Any excess solution falls in a collection sump 36 where it can be extracted through a solution outlet pipe 38 for re-use.

The composition of the solution may be 0.25% antibacterial/antimicrobial agent and 12% excipient with the balance being water but this may vary so that more or less solution has to be applied to the knitted fabric to give a preferred coating of antibacterial/antimicrobial agent of from 0.175 to 0.6 grams per kilogram weight of the knitted fabric. The spray parameters (pressure settings, nozzle characteristics etc.) of the spray guns 32 and the distance between the spray guns and the length of knitted fabric may need to be altered or adjusted depending on the composition of the solution. An example of a suitable solution is the product supplied by Rudolf Chemicals Limited of Alfreton, Derbyshire, United Kingdom under the trade name Rucobac AGP and described in European Patent Application 0734651. The Rucobac AGP product contains a sparingly soluble silver compound deposited on a synthetic oxidic support.

After being sprayed, the length of knitted fabric passes into an enlarged drying chamber 40. The main purpose of the drying chamber 40 is to dry the knitted fabric and remove the bulk of the solution leaving the antibacterial/antimicrobial agent impregnated within the knitted fabric. Air is supplied though an air inlet pipe 20 before being heated by a heater unit (not shown) and fed into the drying chamber 40. Although not shown, the spraying chamber 28 and the drying chamber 40 can be equipped with suitable ventilation and extraction apparatus. The extraction apparatus for the spraying chamber 28 can include removable baffles or filters to remove particles of the antibacterial/antimicrobial agent before venting to atmosphere. The extraction apparatus for the drying chamber 40 is designed to remove any potentially harmful vapour created during the drying process.

Typical processing parameters for Examples 1 and 2 are set out in Table 3 below.

TABLE 3

| Example Number | Total travel time through steaming and drying chambers (seconds) | Travel time through drying chamber (seconds) | Temperature in steaming chamber (° C.) | Temperature in drying chamber (° C.) | Infrared drying lamps |
|---|---|---|---|---|---|
| 1 | 7.5 to 8.5 | 4.8 to 5.8 | 86 | 90 (1 heater element; air intake pipe vent 90° open) | ON |

TABLE 3-continued

| Example Number | Total travel time through steaming and drying chambers (seconds) | Travel time through drying chamber (seconds) | Temperature in steaming chamber (° C.) | Temperature in drying chamber (° C.) | Infrared drying lamps |
|---|---|---|---|---|---|
| 2 | 15 to 17 | 13 to 15 | 86 | 90 (2 heater elements; air intake pipe vent 90° open) | ON |

To accommodate this increased travel time, the length of knitted bandage is wound around a number of static free rolling rollers or pins 42a and 42b such that it is passed back and forth along the length of the drying chamber 40 a number of times, the preferred number being dependent on whether the product is per Example 1 or Example 2. In the case of Example 1 the length of knitted bandage is only passed through the drying chamber a single time. However, the product of Example 2 is a much heavier knitted bandage and absorbs more of the sprayed solution. It therefore requires additional drying time and is preferably passed back and forth along the length of the drying chamber 40 a number of times. FIG. 2 shows the knitted bandage being passed through the drying chamber 40 three times but this is only for the purposes of illustration. The passage of the knitted bandage through the drying chamber 40 can be assisted by driving the rollers or pins 42a and 42b.

A pair of output feed rollers 22 are positioned at the output end of the drying chamber 40 and operate at a given rotational speed. As shown in FIG. 2, there is no tension in the length of knitted fabric 2 as it passes through the steaming chamber 10 the spraying chamber 28 and the drying chamber 40 so that any shrinkage or relaxation of the knitted fabric in the steaming chamber can be easily accommodated.

Additional travel time through the drying chamber 40 can also be achieved by adjusting the rotational speed of the input feed rollers 8 and the output feed rollers 22. However, there is a limit to how much the rotational speed can be adjusted because this also affects the travel time through the steaming chamber 28 and therefore has an effect on the relaxation and wetting of the knitted fabric.

The output feed rollers 22 move the length of knitted fabric into a collecting trough 24 before it is fed into a rolling machine 26. The rolling machine 26 rolls the processed knitted fabric and cuts it into shorter lengths so that the finished knitted bandages can be packaged. A pair of infrared drying lamps 44 is located above the collecting trough 24 to provide additional drying of the knitted fabric after it leaves the drying chamber 40. Like the spray guns 32, the infrared drying lamps 44 can be synchronised with the rest of the steaming and drying apparatus so that they only operate to emit heat when the knitted fabric is being driven through the drying chamber 40.

Experiments

A knitted bandage was prepared using a starting knitted fabric with the properties of Example 1 in Table 1 above and processed using the steaming, spraying and drying apparatus shown schematically in FIG. 2. The spray parameters of the spray guns were selected such that each part of the knitted fabric was sprayed with enough solution to give a coating of Rucobac AGP product that increased the weight of the starting knitted fabric by about 8% (i.e. the wet weight of the knitted bandage after spraying was about 8% higher than the dry weight of the starting knitted fabric). The amount of silver compound in the knitted bandage was calculated by the following method.

A 49 cm$^2$ sample of knitted bandage was cut and placed in a conical flask. 5 mL of sulphuric acid (95%) was added and the conical flask was heated at 250° C. for 20 minutes. 10 mL of nitric acid (68%) was then added and the conical flask was heated at 250° C. for 30 minutes. 5 mL of hydrogen peroxide (50%) was then added a drop at a time and heated at 250° C. for 5 minutes. The solution was transferred to a 50 mL volumetric flask and the conical flask was rinsed with demineralised water. The rinsage liquid was salved in the volumetric flask and completed with demineralised water. A dilution was realised with water acidified with nitric acid at 68%. (For testing purposes the concentration of silver compound must not be higher than 1.5 mg/L to be in the analytical range of the equipment.) The amount of silver compound in the solution was then measured by atomic absorption spectroscopy using an AAnalyst 200 Spectrometer supplied by Perkin Elmer Life and Analytical Sciences Inc, Wellesley, Mass., United States of America and the results were expressed in mg/m$^2$ according to the following formula:

$$\frac{X \times V \times d}{s}$$

where:
X is the result obtained by atomic absorption spectroscopy (mg/L);
V is the volume of the phial in litres (50×10$^3$ L);
d is the dilution; and
s is the surface area of the sample in m$^2$ (49×10$^{-4}$ m$^2$).

The following results were obtained for the knitted bandage prepared using a starting knitted fabric with the properties of Example 1 in Table 1 above and processed using the steaming, spraying and drying apparatus shown schematically in FIG. 2.

TABLE 4

| Sample Number of Example 1 | Silver content (mg/m$^2$) | Average silver content (mg/m$^2$) | Silver content (g/kg weight of knitted fabric) | Average silver content (g/kg weight of knitted fabric) |
|---|---|---|---|---|
| 1 | 0.8 | | 14.8 × 10$^{-3}$ | |
| 2 | 0.7 | | 12.9 × 10$^{-3}$ | |
| 3 | 0.4 | | 7.91 × 10$^{-3}$ | |
| 4 | 0.4 | | 7.51 × 10$^{-3}$ | |
| | | 0.6 | | 10.8 × 10$^{-3}$ |

The knitted bandage was then subjected to a standard dynamic shake method that is designed to evaluate the resistance of non-leaching antimicrobial treated specimens to the growth of microbes under dynamic contact conditions (issued under the fixed designation E 2149 by the American Society for Testing and Materials (ASTM) of West Conshohocken, Pa., United States of America). After a contact time of 24 hours, the knitted bandage was found to give the following reductions:

TABLE 5

| | |
|---|---|
| *Staphylococcus aureus* | >99.9% reduction |
| *Escherichia coli* 0157 | 99.1% reduction |
| *Proteus vulgaris* | 99.9% reduction |
| *Staphylococcus aureus* (resistant strain) | 98.7% reduction |
| *Pseudomonas aeruginosa* | 95.2% reduction |

However, reduction for all of the microbial strains listed above was increased to >99.9% when the spray parameters of the spray guns were selected such that each part of the knitted fabric was sprayed with enough solution to give a coating of Rucobac AGP product that increased the weight of the starting knitted fabric by about 10% in a more uniform manner.

A knitted bandage was prepared using a starting knitted fabric with the properties of Example 2 in Table 1 above and processed using the steaming, spraying and drying apparatus shown schematically in FIG. 2. The spray parameters of the spray guns were selected such that each part of the knitted fabric was sprayed with enough solution to give a coating of Rucobac AGP product of that increased the weight of the starting knitted fabric by about 8%. The amount of silver compound in the knitted bandage was calculated by the method described above. The following results were obtained for the knitted bandage prepared using a starting knitted fabric with the properties of Example 2 in Table 1 above and processed using the steaming, spraying and drying apparatus shown schematically in FIG. 2.

TABLE 6

| Sample Number of Example 2 | Silver content (mg/m²) | Average silver content (mg/m²) | Silver content (g/kg weight of knitted fabric) | Average silver content (g/kg weight of knitted fabric) |
|---|---|---|---|---|
| 1 | 0.9 | | $5.16 \times 10^{-3}$ | |
| 2 | 0.8 | | $4.74 \times 10^{-3}$ | |
| 3 | 1.4 | | $8.84 \times 10^{-3}$ | |
| 4 | 1.5 | | $9.41 \times 10^{-3}$ | |
| | | 1.2 | | $7.04 \times 10^{-3}$ |

The knitted bandage was then subjected to the standard dynamic shake method mentioned above. After a contact time of 24 hours, the knitted bandage was found to give the following reductions:

TABLE 7

| | |
|---|---|
| *Staphylococcus aureus* | >99.9% reduction |
| *Escherichia coli* 0157 | >99.9% reduction |
| *Proteus vulgaris* | 99.9% reduction |
| *Staphylococcus aureus* (resistant strain) | >99.9% reduction |
| *Pseudomonas aeruginosa* | >99.9% reduction |

The invention claimed is:

1. A method of making a bandage from a fabric including the steps of:
    wetting the fabric by steaming the fabric;
    spraying a solution containing an antibacterial/antimicrobial agent directly onto the wetted fabric; and
    drying the sprayed fabric.

2. A method according to claim 1, wherein the bandage is formed from a knitted fabric.

3. A method according to claim 1, wherein the fabric is sprayed to give a coating of antibacterial/antimicrobial agent of from about 0.175 to about 0.6 grams per kilogram weight of the fabric.

4. A method according to claim 1, wherein the fabric is sprayed to give a coating of antibacterial/antimicrobial agent of from about 0.2 to about 0.4 grams per kilogram weight of the fabric.

5. A method according to claim 1, wherein the fabric is sprayed to give a coating wherein an amount of active constituent of the antibacterial/antimicrobial agent is of from about 0.2 to about 2.1 mg/m².

6. A method according to claim 1, wherein the fabric is sprayed to give a coating wherein an amount of active constituent of the antibacterial/antimicrobial agent is of from about 0.4 to about 1.6 mg/m².

7. A method according to claim 1, wherein the fabric is dried at a temperature of between about 80° C. and about 100° C.

8. A method according to claim 1, wherein the fabric is dried at a temperature of about 90° C.

9. A method according to claim 1, wherein the fabric is dried using heated air.

10. An apparatus for making a bandage from a fabric, the apparatus comprising:
    a source of the fabric;
    a steaming chamber through which the fabric passes for wetting the fabric by steaming;
    a spraying chamber through which the wetted fabric passes containing one or more spray guns for spraying a solution containing an antibacterial/antimicrobial agent directly onto the wetted fabric; and
    a drying chamber through which the sprayed fabric passes for drying the fabric after it has been sprayed.

11. An apparatus according to claim 10, wherein the one or more spray guns are compressed air spray guns.

12. An apparatus according to claim 11, wherein the one or more spray guns are located above the fabric so that the solution is sprayed onto an upper surface of the fabric.

13. An apparatus according to claim 10, wherein the spraying chamber further comprises one or more spray guns located below the fabric so that the solution is sprayed onto a lower surface of the fabric.

14. An apparatus according to claim 10, wherein the spraying chamber includes a collection sump for receiving excess solution.

15. An apparatus according to claim 10, wherein the spraying chamber includes a roller for supporting the fabric.

16. An apparatus according to claim 10, wherein the fabric is sprayed to give a coating of antibacterial/antimicrobial agent of from about 0.175 to about 0.6 grams per kilogram weight of the fabric.

17. An apparatus according to claim 10, wherein the fabric is sprayed to give a coating of antibacterial/antimicrobial agent of from about 0.2 to about 0.4 grams per kilogram weight of the fabric.

18. An apparatus according to claim 10, wherein the fabric is sprayed to give a coating wherein an amount of active constituent of the antibacterial/antimicrobial agent is of from about 0.2 to about 2.1 mg/m².

19. An apparatus according to claim 10, wherein the fabric is sprayed to give a coating wherein an amount of active constituent of the antibacterial/antimicrobial agent is of from about 0.4 to about 1.6 mg/m².

20. An apparatus according to claim 10, wherein the temperature in the drying chamber is between about 80° C. and about 100° C.

21. An apparatus according to claim 10, wherein the temperature in the drying chamber is about 90° C.

22. A bandage consisting of a fabric wherein the fabric contains an amount of antibacterial/antimicrobial agent of from about 0.175 to about 0.6 grams per kilogram weight of the fabric.

23. A bandage according to claim 22, wherein the fabric contains an amount of antibacterial/antimicrobial agent of from about 0.2 to about 0.4 grams per kilogram weight of the fabric.

24. A bandage according to claim 22, wherein an amount of active constituent of the antibacterial/antimicrobial agent is of from about 0.2 to about 2.1 mg/m$^2$.

25. A bandage according to claim 22, wherein an amount of active constituent of the antibacterial/antimicrobial agent is of from about 0.4 to about 1.6 mg/m$^2$.

26. A bandage according to claim 22, wherein the fabric is a knitted fabric.

27. A bandage according to claim 22, wherein the fabric is steamed before being sprayed with a solution containing the antibacterial/antimicrobial agent.

28. A bandage according to claim 22, wherein the fabric is dried after being sprayed with a solution containing the antibacterial/antimicrobial agent.

* * * * *

UNITED STATES PATENT AND TRADEMARK OFFICE
CERTIFICATE OF CORRECTION

| | | |
|---|---|---|
| PATENT NO. | : 8,168,849 B2 | |
| APPLICATION NO. | : 12/089332 | |
| DATED | : May 1, 2012 | |
| INVENTOR(S) | : David Timothy Baldock | |

It is certified that error appears in the above-identified patent and that said Letters Patent is hereby corrected as shown below:

Column 8, Line 44
$(50 \times 10^3 L)$ should read $(50 \times 10^{-3} L)$

Signed and Sealed this
Twenty-ninth Day of January, 2013

David J. Kappos
*Director of the United States Patent and Trademark Office*